United States Patent [19]
Potts

[11] Patent Number: 5,840,953
[45] Date of Patent: Nov. 24, 1998

[54] PURIFIED TETRAETHOXYSILANE AND METHOD OF PURIFYING

[75] Inventor: Thomas M. Potts, Joplin, Mo.

[73] Assignee: Eagle-Picher Industries, Inc., Cincinnati, Ohio

[21] Appl. No.: 558,682

[22] Filed: Nov. 16, 1995

[51] Int. Cl.⁶ ................................................ C07F 07/04
[52] U.S. Cl. ........................ 556/483; 95/84; 95/86; 95/88
[58] Field of Search ................. 556/483; 95/84, 95/86, 88

[56] References Cited

U.S. PATENT DOCUMENTS

| | | |
|---|---|---|
| 2,972,626 | 2/1961 | Marota . |
| 3,002,583 | 10/1961 | Findlay . |
| 3,019,087 | 1/1962 | Jacob et al. . |
| 3,041,141 | 6/1962 | Shoemaker et al. . |
| 3,118,947 | 1/1964 | Amir . |
| 3,267,646 | 8/1966 | Kauss et al. . |
| 4,003,257 | 1/1977 | Fletcher et al. . |
| 4,070,444 | 1/1978 | Ingle . |
| 4,159,966 | 7/1979 | Roberts . |
| 4,447,632 | 5/1984 | Mallon . |
| 4,532,120 | 7/1985 | Smith et al. . |
| 4,537,759 | 8/1985 | Walker et al. . |
| 4,772,296 | 9/1988 | Potts . |
| 5,069,690 | 12/1991 | Henderson et al. . |
| 5,260,470 | 11/1993 | Goebel et al. . |

FOREIGN PATENT DOCUMENTS

| | | |
|---|---|---|
| 2139155 | 2/1973 | Germany . |
| 45-36203 | 11/1970 | Japan . |
| 49-54298 | 5/1974 | Japan . |
| 59-30711 | 2/1984 | Japan . |
| 802339 | 10/1958 | United Kingdom . |

OTHER PUBLICATIONS

Article entitled "Alkyl Orthosilicates" by A. W. Dearing and E. Emmet Reid, American Chemical Soc., vol. 50, pp. 3058–3062, 1928.

Chemical Abstracts, vol. 119, No. 21, Nov. 1993, Columbus, Ohio, US;.

Abstract No. 226187d, Onozawa, K. et al.; "Purification of organic silicon compounds useful in super large scale integrated circuits".

*Primary Examiner*—Paul F. Shaver
*Attorney, Agent, or Firm*—Wood, Herron & Evans, L.L.P.

[57] ABSTRACT

Tetraethoxysilane is purified by passing impure material through a gas chromatographic separating column at a temperature below the boiling point of the pure tetraethoxysilane. Separation of pure material from impurities occurs on the column, and the pure material is thereafter cooled and collected in a receiver. The purified tetraethoxysilane has 99.999999% purity based on metals content.

10 Claims, 3 Drawing Sheets

PURIFIED TETRAETHOXYSILANE AND METHOD OF PURIFYING

FIELD OF THE INVENTION

The invention relates to a process for producing tetraethoxysilane of ultra high purity with decreased risk of decomposition during removal of impurities, and the purified tetraethoxysilane made by this process.

BACKGROUND OF THE INVENTION

Tetraethoxysilane, also known as tetraethylorthosilicate (TEOS), with the structure $Si(OC_2H_5)_4$, is used extensively in chemical vapor deposition reactors in connection with the formation of silicon dioxide ($SiO_2$) films onto a substrate for the manufacture of semiconductor devices. Silicon dioxide forms the insulating surface of the semiconductor device. In this application, TEOS must be as free of impurities as possible to form silicon dioxide films of acceptable electronic properties. TEOS is also used in the manufacture of products such as silicon gels, paints and plastics, but high purity is not as important in these applications.

TEOS is a liquid at room temperature, and boils at approximately 167° C., according to the Handbook of Chemistry and Physics listed range of 165.5°–168° C. (CRC Press, 74th Edition). Unfortunately, during atmospheric pressure distillation TEOS tends to decompose to ethanol, silicon dioxide, and various polymers believed to be oligomeric silyl ethers, as the material approaches the boiling point temperature. This characteristic of TEOS has inhibited efforts to obtain very highly purified product.

Typically, TEOS upon initial manufacture is approximately 97% pure. The impurities include electronically active materials such as metallics or metalloids, which in 97% pure TEOS are present at a concentration of about 1 to 5 parts per million (ppm). These impurities deposited onto a silicon dioxide film can drastically alter the electronic properties of the film rendering the semiconductor device useless. Electronically active impurities must be reduced to less than 1 part per billion (ppb) for the silicon dioxide film to be useful. The nonelectronic impurities in TEOS include organic materials and water. These impurities adversely affect the film's physical properties by altering the structural integrity and planar uniformity of the film surface.

Presently available purification techniques, such as low pressure distillation, can increase the purity of the TEOS to approximately 99.8%. Of course, even at this purity level, there are still approximately 0.2% impurities in the TEOS and a portion of these impurities will be deposited onto a film layer made from the TEOS. The presence of the nonelectronic impurities in the film interrupts the planar uniformity and results in stress points which can alter both the structural and electronic integrity of the film. Additionally, the amount of depositable electronically active impurities remaining in the conventionally purified TEOS still can equal, and possibly exceed, the amount of dopant which is introduced into the silicon dioxide film for tailoring the electronic properties.

It would be highly advantageous to have a purification method for TEOS which would substantially decrease the amount of electronic and nonelectronic impurities which could potentially be deposited onto a silicon dioxide film used for semiconductor device manufacture. Further, it would be highly advantageous to have TEOS in an ultra-purified state which would permit manufacture of silicon dioxide films with electronic properties substantially unaffected by any impurity present as a component of the TEOS.

It would be yet a further advantage to have a device which can provide an environment for effecting separation of TEOS from both its electronically active and nonelectronic impurities.

SUMMARY OF THE INVENTION

The invention relates to a process for purifying TEOS, the purified product, and the equipment for effecting purification. TEOS can be purified in a manner which will produce a product comprising up to 99.9999% TEOS. The process utilizes large-scale gas chromatography (LSGC) with injection of the raw TEOS as a series of timed, spaced pulses into a carrier gas stream which transports the TEOS pulses to a gas chromatographic column, through which the pulses flow in sequence. The column utilizes a non-polar packing to allow impurities such as ethanol to elute during a gap between the pulses.

Water is also typically present in the raw TEOS as an impurity. It is believed that the present process causes a reaction between the raw TEOS and water present as an impurity within the column to form ethanol and polymeric silyl ethers. Both of these reaction products elute from the column apart from the purified TEOS. Some of the polymeric silyl ethers may be retained on the column. Thus, the process removes water not strictly by a separation technique, but also by being consumed via reaction with TEOS in the column.

TEOS is known to interact with many materials commonly used in fabricating storage and transfer equipment, such as steel, nickel, chromium, aluminum, zinc, and brass, especially at temperatures approaching the boiling point of TEOS. Thus, reaction could occur inside the gas chromatograph when steel components come into contact with the TEOS. To address this problem, the surfaces which TEOS contacts in the chromatograph are fabricated from inert materials such as TEFLON. Alternatively, reactive fabrication materials can be protected by lining with an inert material, such as by lining steel with TEFLON. Gold plating of the contact surfaces of brass components has also proven successful in resisting TEOS attack. Though expensive as a fabricating material, titanium can be used without separate surface treatment for fabricating component parts.

One feature of the process is that though the gas chromatograph operates essentially at atmospheric pressure, TEOS is purified by conducting the raw materials through a separating column heated to a temperature below the boiling point of TEOS. Normally, a material to be purified in a LSGC is heated to above the boiling point at atmospheric pressure and passed through the chromatographic column in the vapor phase. In purifying a material such as TEOS through the LSGC, the operating temperature is maintained below the boiling point of TEOS at atmospheric pressure to minimize decomposition. Thus, as a pulse of TEOS passes through the separating column at least a portion of the TEOS pulse is in the liquid phase.

It is contemplated that the technique of purifying a material such as TEOS with at least a portion of the TEOS in the liquid phase would also be feasible where at least a partial vacuum would be created in the separating column which would effectively lower the actual boiling point of TEOS.

Under at least partial vacuum conditions in the separating column, it is further contemplated as an alternative embodiment that purification of the TEOS with insignificant decomposition can be effected with the TEOS entirely in the vapor state. However, the resolution, TEOS processing rate, or both, may be somewhat depressed when the TEOS in the separating column is present entirely as a vapor.

DETAILED DESCRIPTION OF THE INVENTION

Figure 1:
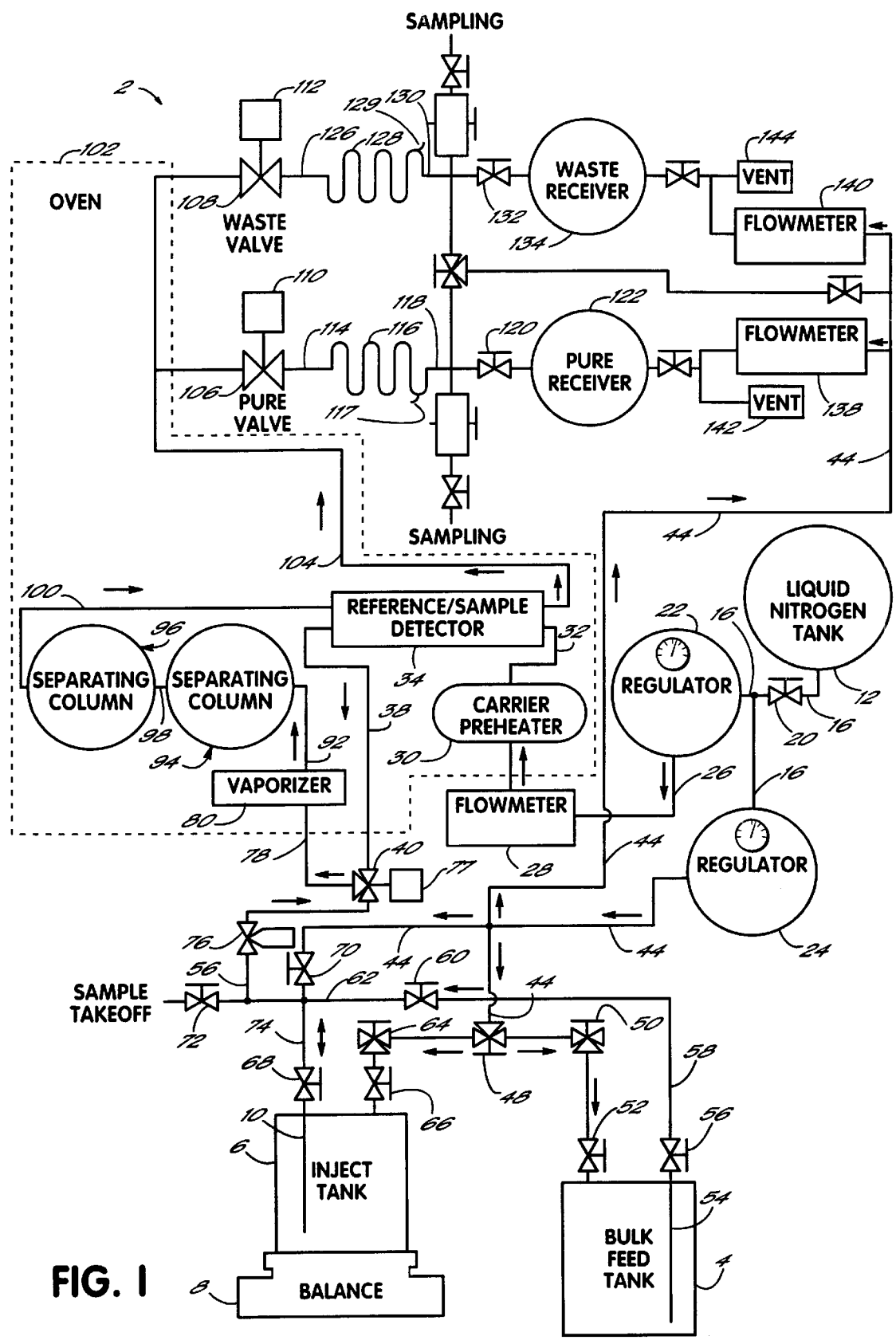
FIG. 1 is a flow diagram of a TEOS purification system in accordance with a preferred embodiment of the invention.

The invention in its broader aspects relates to a method of purifying tetraethoxysilane, comprising injecting impure tetraethoxysilane in the gaseous phase into a gas chromatograph column as a series of spaced pulses, heating the gas chromatograph column to a temperature less than the boiling point of pure tetraethoxysilane, passing the impure tetraethoxysilane through the gas chromatograph column by a flow of carrier gas, separating impurities in the impure tetraethoxysilane from purified tetraethoxysilane which results in elution of purified tetraethoxysilane from the gas chromatograph column at a different time than the impurities, and receiving the purified tetraethoxysilane at a location distinct from that of the impurities. Alternatively, purification of TEOS without significant decomposition may be effected in at least a partial vacuum where all the TEOS in the separating column is present in the vapor state. It is believed that the process of purifying a material in a gas chromatograph column at a temperature below the boiling point of the material can be beneficially practiced on materials other than tetraethoxysilane.

The invention also relates to the purified tetraethoxysilane produced by this process, which is orders of magnitude purer than that which is conventionally obtainable. The resulting purified tetraethoxysilane has up to two orders of magnitude fewer metallic impurities than conventionally available purified product, allowing improved silicon dioxide thin films to be manufactured, such as for semiconductor devices. The use of the TEOS purified by this process increases the device yield on the wafers used for device fabrication because of the reduced impurities compared to other silicon dioxide sources and TEOS of lesser purity.

The invention also relates to the construction of the separating column component, which provides for a uniform flow of the TEOS pulse along the length of the column to optimize separation of impurities from the TEOS.

The following discussion relates to the purification of TEOS using the inventive process. In referring to the figures, a number of elements will be discussed. A listing of those elements and identifying numbers is provided below.

| Element | Number |
|---|---|
| Purification System | 2 |
| Bulk Feed Tank | 4 |
| Inject Tank | 6 |
| Balance | 8 |
| Liquid $N_2$ Storage Tank | 12 |

-continued

| Element | Number |
|---|---|
| $N_2$ Supply Line | 16 |
| Tank Valve | 20 |
| Carrier Gas Regulator | 22 |
| $N_2$ Pressurization Regulator | 24 |
| Carrier Gas Line | 26 |
| Flow Meter | 28 |
| Carrier Gas Preheater | 30 |
| Preheater Line | 32 |
| Detector | 34 |
| Detector Outlet Line | 38 |
| 3-Way Injector Valve | 40 |
| $N_2$ Pressurization Line | 44 |
| 3-Way Selector Valve | 48 |
| Bulk Feed Tank Pressurization Valve | 50 |
| Bulk Feed Tank Inlet Valve | 52 |
| Dip Tube | 54 |
| Bulk Feed Tank Liquid Valve | 56 |
| Transfer Line | 58 |
| Valve | 60 |
| TEOS Transfer Line | 62 |
| Inject Tank Pressurization Valve | 64 |
| Inject Tank Inlet Valve | 66 |
| Inject Tank Liquid Valve | 68 |
| Pressurization Valve | 70 |
| Sample Takeoff Valve | 72 |
| Transfer Line | 74 |
| Metering Valve | 76 |
| Computer-Regulated Controller | 77 |
| Vaporizer Inlet Line | 78 |
| Vaporizer | 80 |
| Titanium Pipe | 82 |
| Aluminum Cylinder | 84 |
| Cartridge Heater Well | 88 |
| Thermocouple Well | 90 |
| Vaporizer Outlet Line | 92 |
| Separating Column | 94 |
| Separating Column | 96 |
| Connector Line | 98 |
| Column Outlet Line | 100 |
| Oven | 102 |
| Transfer Line | 104 |
| Pure Valve | 106 |
| Waste Valve | 108 |
| Pure Valve Controller | 110 |
| Waste Valve Controller | 112 |
| Connector Line | 114 |
| Condenser | 116 |
| Tube Bundle | 116a |
| Vent Line | 117 |
| Condenser Outlet Line | 118 |
| Valve | 120 |
| Pure TEOS Receiver | 122 |
| Connector Line | 126 |
| Condenser | 128 |
| Vent Line | 129 |
| Condenser Outlet Line | 130 |
| Valve | 132 |
| Waste Receiver | 134 |
| Flow Meter | 138 |
| Flow Neter | 140 |
| Vent | 142 |
| Vent | 144 |
| Column Member | 200 |
| PTFE Liner | 202 |
| Column Plug | 204 |
| Titanium Flange | 206 |
| TEFLON Block | 208 |
| Flange | 210 |
| O-Ring | 214 |
| Circumferential Groove | 218 |
| PYREX Frit | 220 |
| Frit Receptacle | 224 |
| Aperture | 228 |
| Conical Space | 230 |
| Conical Space | 230a |
| Solid Support | 236 |

FIG. 1 depicts the purification system 2. In normal operation, the raw TEOS of about 97% purity is originally stored in bulk feed tank 4. TEOS is then transferred to inject tank 6, which is used to supply the raw TEOS to be purified and also for the purpose of setting valves downstream and for calibrating the injection weight of the raw TEOS. The inject tank 6 is positioned on a balance 8 for assisting in evaluating the above metering functions. Raw TEOS flows into the inject tank 6 through inject tank dip tube 10, and thereafter downstream through the same inject tank dip tube 10 by appropriate valve adjustment. The inject tank 6 includes an external heater (not shown) to warm the raw TEOS to about 90° C. before transfer is begun.

A gas inert to TEOS, the column and system components is utilized as a carrier gas in the purification system 2. Nitrogen has been successfully used as the carrier gas, though other inert gases may also be employed. The source for the nitrogen carrier gas is the liquid nitrogen storage tank 12. Nitrogen as a gas flows into the nitrogen supply line 16 through tank valve 20 and along nitrogen supply line 16 to carrier gas regulator 22 and nitrogen pressurization regulator 24.

Nitrogen gas at the carrier gas regulator 22 is stepped down to about 15–50 psig and passes through carrier gas line 26 into flow meter 28. For a four inch (10.2 cm) outside diameter separating column, the pressure range is maintained by the gas regulator 22 at about 20 to 25 psig. The rate of flow of the carrier gas is controlled by flow meter 28. The preferred flow rate is established using a Van Deemter plot, which displays the height equivalent to a theoretical plate (HETP) versus the carrier flow. For production gas chromatography, optimum flow rates are about 2 to about 2.5 times higher than optimum rates for analytical gas chromatography. For a 10.2 cm diameter production column, the optimum flow rate is in the range of about 15 to about 20 liters per minute. Thereafter, the carrier gas flows into carrier gas preheater 30, which increases the nitrogen gas temperature to that of the separating column. Heated nitrogen gas exits the carrier gas preheater 30 through preheater line 32 and into detector 34. Detector 34 functions by comparing a reference signal to a sample signal, the reference signal being provided by the pure nitrogen carrier gas.

The carrier gas exits detector 34 through detector outlet line 38 and is introduced into the separating column portion of the purification system 2 via three-way injector valve 40.

Nitrogen gas at the nitrogen pressurization regulator 24 is stepped down to 40 psig and transferred along nitrogen pressurization line 44. The nitrogen is caused to enter either but not both of bulk feed tank 4 and inject tank 6 by appropriate setting of three-way selector valve 48. To pressurize bulk feed tank 4, bulk feed tank pressurization valve 50 and bulk feed tank inlet valve 52 are opened. Nitrogen gas at 40 psig enters the bulk feed tank 4 and forces the raw TEOS through dip tube 54 and opened bulk feed tank liquid valve 56.

Raw TEOS then passes along transfer line 58, through valve 60 and TEOS transfer line 62, through inject tank dip tube 10, and into inject tank 6. By opening pressurization three way valve 64 and inject tank inlet valve 66 and properly adjusting inject tank liquid valve 68, pressurization valve 70 and sample takeoff valve 72, TEOS from the inject tank 6 can be caused to flow into transfer line 74, through metering valve 76, and thereafter into three-way injector valve 40. The three-way injector valve 40 is switchable to allow downstream flow of either raw TEOS or carrier gas, but not both simultaneously. The three-way injector valve 40, controlled by computer-regulated controller 77, permits flow of raw TEOS into vaporizer inlet lines 78 as a series of timed pulses, between which the carrier gas is caused to flow. The raw TEOS transfer lines and valves downstream of inject tank 6 are maintained at an elevated temperature between about 50° and 100° C., preferably about 95° C., to limit the amount of additional heat needed to vaporize the TEOS.

Figure 2:
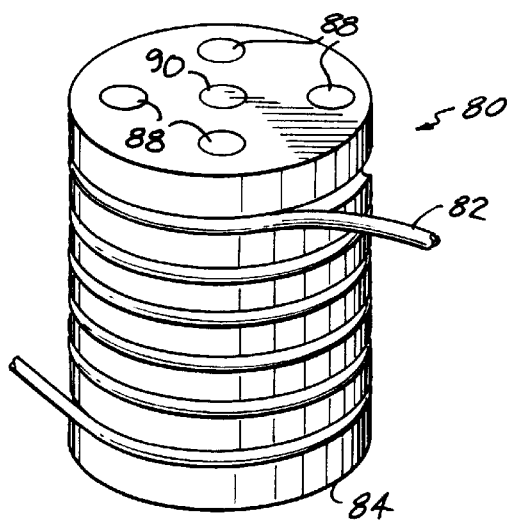
FIG. 2 is a perspective view of the vaporizer component of the purification system.

The vaporizer 80 is located downstream of the three-way injector valve 40. Preferably, the vaporizer 80 is fabricated from a titanium pipe 82 coiled around a cylinder of aluminum 84. FIG. 2, not drawn to scale, shows the construction of the vaporizer 80. Aluminum cylinder 84 has a U-bottomed groove machined in its surface. The groove is sized to receive the titanium pipe 82 for maximum heat conductivity. Four cartridge heater wells 88 are bored along the length of the aluminum cylinder 84 to accept individual cartridge heaters (not shown). The power of these heaters must be sized according to the amount of TEOS injected. Currently, 250 watt heaters are used. A thermocouple well 90 is also bored along the length of aluminum cylinder 84 to accept a thermocouple (not shown). The cartridge heaters and thermocouple in turn are connected to a temperature controller, not shown, which maintains the temperature of the aluminum cylinder 84 typically at about 170° C., above the atmospheric pressure boiling point of pure TEOS. The outside diameter of the aluminum cylinder 84, and thus the approximate diameter of the titanium coil 82 is nine inches (22.8 cm).

Vaporized TEOS exits the vaporizer 80 through vaporizer outlet line 92 and enters separating column 94. For large scale chromatographic separation purposes, the outside diameter of the column is relatively large, approximately 10.2 centimeters. At this diameter, it is difficult to coil the column. Thus, to attain sufficient separating column length in a restricted oven dimension, multiple columns are aligned in series. Two columns have been successfully utilized in series. Column length and diameter are selected to optimize separation efficiency relative to throughput. Often these variables of column length and diameter are determined empirically. After exiting separating column 94, the TEOS pulse or carrier gas enters the second separating column 96 through connector line 98.

Figure 3:
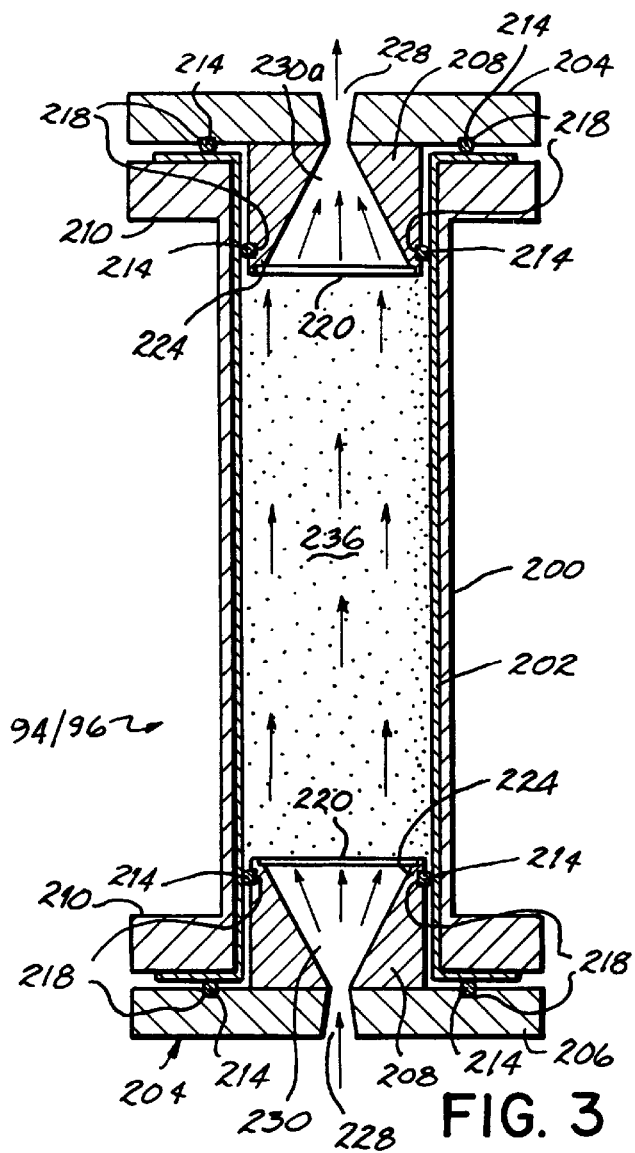
FIG. 3 is a side elevational view of the separating column component of the purification system.

As shown in more detail in FIG. 3, separating column 94/96 is comprised of a 300 psi carbon steel column member 200 ⅛ inch (0.32 cm) thick along the length of the column member 200 lined with a ⅛ inch (0.32 cm) thick polytetrafluoroethylene (TEFLON) liner 202. The column member 200 is manufactured by PSI, Charleston, W.Va. At both ends of the column member 200 are column end plates 204 each comprised of a grade 2 titanium blank pipe flange 206 and one piece TEFLON block 208 which are maintained in contact by a pressure fit. The flange 210 of column member 200, approximately ½ to ¾ inch (1.29 to 1.90 cm) in thickness, is secured in position relative to the mating titanium blank pipe flange 206 by eight bolts (not shown) fitted through evenly-spaced holes (not shown) around the circumference of the titanium block pipe flange 206 and flange 210. TEFLON O-rings 214 are fitted into circumferential grooves 218 machined both on one face of the titanium flange 206 and the circumference of TEFLON block 208. A circular PYREX frit 220 from Ace Glass, Louisville, Ky., with an 83 mm diameter and 6 mm thickness with porosity B, is fitted into frit receptacle 224 at the end of TEFLON block 208. The aperture 228 in the titanium pipe flange 206 is a 0.25 inch (0.64 cm) machined NPT female fitting. The conical space 230 behind the PYREX frit 220 is shaped to allow for expansion of the vaporized gas upstream of the solid support 236 in the column member 200 so that the vaporized gas passes throughout the upstream PYREX frit 220 substantially in plug flow. Vaporized gas in this orientation permits optimized separation of impurities from the TEOS as the gas/liquid flows through the solid support 236. The conical space 230a downstream of the solid support 236 utilizes the same design but as the reverse of the upstream conical space 230 to effectively funnel the separated components off the column for transporting downstream.

Figure 5:
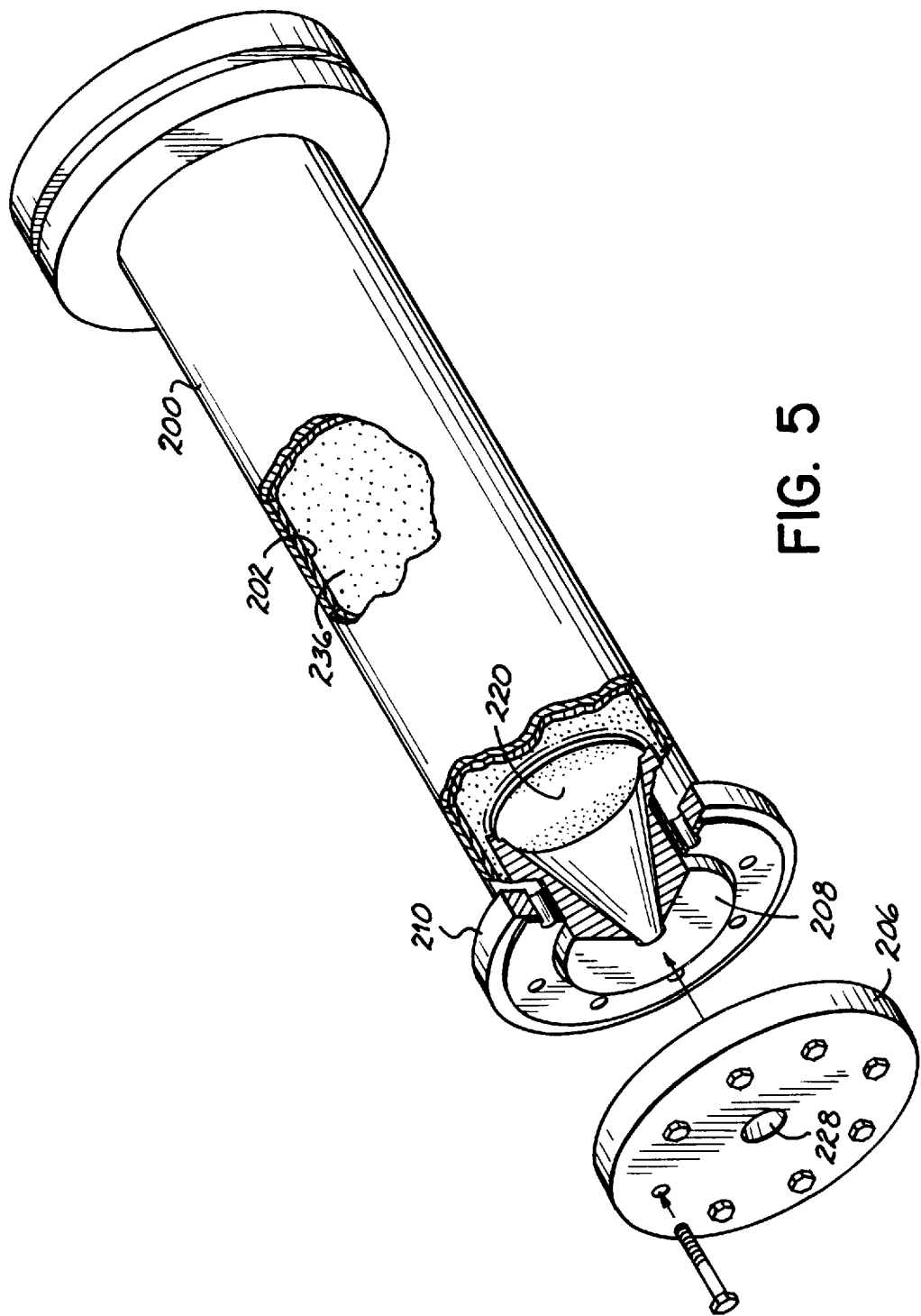
FIG. 5 is a disassembled partially broken away perspective view of the separating column.

FIG. 5 provides another view of the separating column 94/96, further showing the means for securing the titanium blank pipe flange 206 to flange 210.

This construction arrangement of the separating column 94/96 has proven effective in connection with purifying TEOS, but is also expected to demonstrate beneficial effects in the separation of impurities from a range of other materials.

To facilitate removal of water from TEOS, the solid support 236 can optionally include approximately a 3 inch (7.6 cm) layer of granular UHP grade lithium hydride (LiH) at the upstream end of the column 94. The lithium hydride layer reacts with water to form lithium hydroxide and hydrogen gas. The lithium hydroxide remains in the column, while the hydrogen gas passes through columns 94 and 96 at a different rate than TEOS and is ultimately vented. TEOS is thus dried without introducing an interfering impurity.

For separating the TEOS component of raw TEOS from the impurities, separating columns 94 and 96 are packed with a solid support, such as diatomaceous earth, having a particle size in the range of 80–100 mesh (175-147 microns). This particle size range provides the desired removal of impurities from TEOS while maintaining an acceptable throughput. Thus, a solid support with a particle size of 60–80 mesh (250-175 microns) provides greater throughput but lower purity; a smaller particle size solid support of 100–120 mesh (147-130 microns) provides lower throughput and higher purity. It is expected that additional solid support materials, such as silica, activated carbon, glass beads, and porous polymers, would be effective in this application.

The diatomaceous earth is coated with silicone oil such as OV-101 available from Ohio Valley Specialty Chemicals, Marietta, Ohio, to a concentration of 10% oil by total weight of the earth and oil. Separation of components in the impure TEOS using the above diatomaceous earth/silicone oil combination occurs by a liquid-gas mechanism. However, another mechanism by which separation of components can occur in the separating columns 94/96 involves a gas-solid mechanism wherein molecules from the impure TEOS are held on the surface of a solid support, typically by ionic attraction. Also, the molecules from the impure TEOS may be differentially retained inside pores of a solid support such as a zeolite.

The temperature of the separating columns 94 and 96 is maintained at approximately 145° C. This temperature is insufficient to maintain the raw TEOS completely in the vapor state at atmospheric pressure. The combination of carrier gas flow and temperature is nonetheless sufficient to maintain at least a portion of the TEOS as a vapor. The remaining TEOS is present in the separating columns 94/96 as a liquid, which is in turn revaporized, brought into contact with the silicone oil, dissolved, desolvated from the silicone oil, and passed further down the column. Operating the separating columns 94 and 96 at a temperature below the boiling point of the TEOS has been found to minimize decomposition risk of the TEOS. The separation efficiency of the liquid phase on the diatomaceous earth has been found to be dependent on the liquid phase composition. Good results have been obtained using the above OV-101 silicone oil. However, other materials commonly used as the liquid phase on a solid support, such as other silicone oils, waxes or gum rubbers, could be used.

The 80–100 mesh diatomaceous earth is of a smaller size than typically used in large scale preparative chromatography. Better separation efficiency has been obtained using this finer mesh diatomaceous earth, in combination with the thin layer of silicone oil. The oil coating is thinner than with coarser diatomaceous earth particles per weight concentration because of the increased surface area of the finer particles. Nonetheless, this thin coating of silicone oil OV-101 further assists in improving separation efficiency. A coating of oil at 10% by total weight of the oil and diatomaceous earth has proven effective. Nonetheless, lower oil coating weights, in the range of about 5% to about 10%, may also be used.

The purified TEOS, impurities and carrier gas separately exit separating column 96 and enter column outlet line 100. Because the TEOS reacts vigorously with stainless steel at elevated temperatures, the column outlet line 100 is fabricated from titanium or other nonreactive material. The temperature of the material inside column outlet line 100 is maintained at about 145° C. Column outlet line 100 passes through detector 34, which is capable of providing a signal indicating the presence of a material other than the carrier gas at that point in the system. Column outlet line 100, the separating columns 94 and 96, and certain other heated system components are housed within oven 102, as shown in FIG. 1.

Downstream of the detector 34 is transfer line 104 which conveys the separated materials from separating column 96 either to pure valve 106 or waste valve 108. These valves are respectively controlled by valve controllers 110 and 112.

Figure 4:
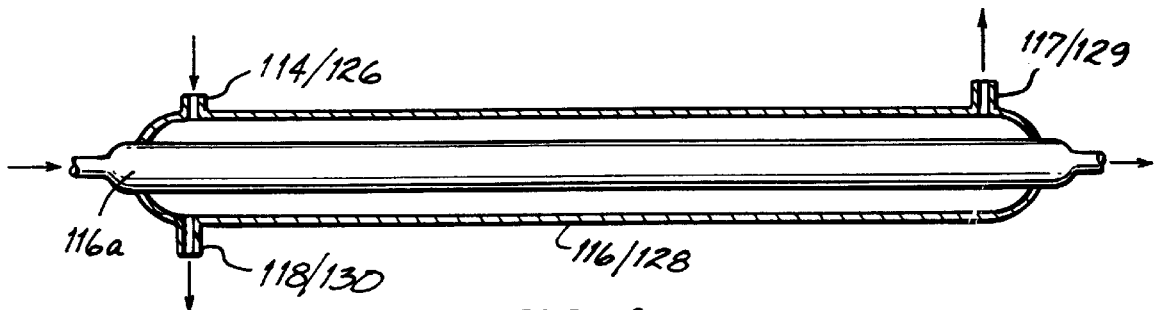
FIG. 4 is a side view of the condenser component of the purification system.

Downstream of pure valve 106 is an air-cooled connector line 114. Because of the temperature of the purified TEOS at this point, the connector line 114 must be made of titanium or other material nonreactive to hot TEOS. The air-cooled connector line 114 allows the TEOS therein to cool to approximately 90° C. The TEOS then enters condenser 116, shown in more detail in FIG. 4. The condenser 116 is commercially available as Model 3036, ITT Standard, Buffalo, N.Y. Condenser 116 utilizes a mixture of ethylene glycol and water cooled to approximately −20° C. and introduced into the tube bundle 116a of the condenser 116 to cool the TEOS surrounding the tube bundle 116a to approximately room temperature. Because the TEOS has been brought to a lower temperature in the line 114, condenser 116 can be made from stainless steel. The gaseous fraction passing through condenser 116 is carrier gas, which is vented through vent line 117 as shown in FIGS. 1 and 4. The liquid portion from condenser 116 flows through condenser outlet line 118, through valve 120 and into pure TEOS receiver 122.

During that portion of the separation cycle where waste material is exiting the separating column 96, waste valve 108 is opened by waste valve controller 112 while pure valve 106 remains closed. A mixture of carrier gas, residual TEOS, organic and organometallic impurities, and other impurities flow through transfer line 104 and waste valve 108 into connector line 126 and thereafter condenser 128. Connector line 126 and condenser 128 are fabricated in the manner substantially identical to that for connector line 114 and condenser 116. The gaseous component of the material entering condenser 128 through waste valve 108 is comprised of carrier gas and various high vapor pressure organic materials. Water vapor may also be present. This gaseous component is vented through vent line 129. The liquid fraction exiting condenser 128 flows through condenser outlet line 130, through valve 132 and into waste receiver 134.

To eliminate the risk of air contamination of the purified TEOS, a carrier gas flow downstream of regulator 24 through nitrogen pressurization line 44 provides a trickle nitrogen flow at a rate less than 1 liter/minute through flow meters 138 and 140 to provide a positive pressure flow respectively through vents 142 and 144. In this manner, air cannot backflow into the vents 142 and 144 and provide a risk of air contamination into pure receiver 122.

A purification system of the type described above was fabricated, utilizing as separating columns two four-foot (1.22 m) columns having an outside diameter of approximately 10.2 centimeters. Purification was initiated by injecting 150 grams of raw TEOS from inject tank 6 through injection valve 40 over seven seconds. The pressurization gas and carrier gas was nitrogen. Typically, the waste valve 108 is open and pure valve 106 is closed in the initial seven seconds of the injection. After the raw TEOS injection was discontinued, waste valve 108 was maintained open from the eighth second through 205 seconds and pure valve 106 closed. During this time, carrier gas only through injection valve 40 behind the injected plug of raw TEOS. From 206 through 340 seconds, the pure valve 106 was opened to receive the purified plug of TEOS and waste valve 108 closed. At 341 through 360 seconds, the waste valve 108 was opened and the pure valve 106 was closed to permit passage of any heavy impurities eluting slowly from the separating columns 94 and 96 through waste valve 108. The cycle then repeated with another seven-second injection of raw TEOS. In the second and later injections of raw TEOS, during the eighth second through 205 seconds, the remainder of heavy impurities from the earlier injection continued to elute from the separating columns 94 and 96, along with the light impurities from the later injection of raw TEOS. Typically during raw TEOS injection, waste valve 108 is open, and pure valve 106 closed.

In the above operating example, separation control involving the opening and closing of specific valves is exclusively time based, as long as all other operational parameters remain constant. It is possible that sensor-based separation control can be achieved.

The operational parameters for a preparative gas chromatograph are the column packing, column length, flow rate of the carrier gas, the composition of the carrier gas, the temperature of the column, the injection rate of the raw TEOS, and the injection time of the raw TEOS. It can be appreciated that the timing sequence for opening and closing pure and waste valves 106 and 108 will be dependent on the above parameters as well as the dimensions of the component parts of the purification system 2. Thus, the appropriate timing sequence will best be determined empirically after the above operational parameters are selected and set.

Operating the purification system under the above parameters, approximately 28 kilograms of TEOS of 99.999999% purity on the basis of metals content were produced in a 24 hour period. Testing for the presence of thirty standard metals showed each metal content to be less than 1 ppb. A gas chromatograph assay of the purified TEOS showed 100% purity, with an estimated detection limit of 0.01%. The moisture content was less than 2 ppm, the instrument detection limit. A particle analysis of the purified TEOS showed no particles in the sample, the detection limit being greater than 0.3 microns. TEOS purified by this method significantly exceeds the SEMI C7.1395 guidelines for tetraethylorthosilicate, Tier A. Separation of impurities from TEOS is achieved in a manner which minimizes the risk of decomposition of the TEOS, while optimizing purity and production rate.

This specification has described the present invention and its operating parameters. Variations may be achieved without departing from the spirit and scope hereof as defined by the claims.

What is claimed is:

1. A method of purifying tetraethoxysilane, comprising:
   injecting impure tetraethoxysilane in the gaseous phase into a gas chromatograph column as a series of spaced pulses;
   heating said gas chromatograph column to a temperature less than the boiling point of pure tetraethoxysilane;
   passing said impure tetraethoxysilane through said gas chromatograph column by a flow of carrier gas;
   separating impurities in said impure tetraethoxysilane from purified tetraethoxysilane which results in elution of purified tetraethoxysilane from said gas chromatograph column at a different time than said impurities; and
   receiving said purified tetraethoxysilane at a location distinct from that of said impurities.

2. The method of claim 1 wherein said gas chromatograph column is heated to a temperature in the range of about 70° to about 165° C.

3. The method of claim 1 wherein said gas chromatograph column has a diatomaceous earth column packing.

4. The method of claim 3 wherein said diatomaceous earth column packing has a particle size in the range of about 80 to about 100 mesh.

5. The method of claim 3 wherein said diatomaceous earth is coated with about 10% by weight silicone oil.

6. The method of claim 1 further comprising removing water from said impure tetraethoxysilane by passing said impure tetraethoxysilane through a water-removing material.

7. The method of claim 6 wherein said water-removing material is lithium hydride.

8. A purified tetraethoxysilane compound produced according to the method of claim 1.

9. Tetraethoxysilane as a discrete compound having a purity as determined by metals analysis of at least 99.999999%.

10. Tetraethoxysilane of claim 9 further wherein moisture content of said tetraethoxysilane is less than 2 parts per million.

* * * * *